(12) United States Patent
McNair (10) Patent No.: US 11,357,444 B1
(45) Date of Patent: Jun. 14, 2022

(54) DETERMINING PATIENT CANDIDACY FOR EPILEPSY NEUROSURGICAL PROCEDURE

(71) Applicant: CERNER INNOVATION, INC., Kansas City, KS (US)

(72) Inventor: Douglas S. McNair, Leawood, KS (US)

(73) Assignee: CERNER INNOVATION, INC., North Kansas City, MO (US)

( * ) Notice: Subject to any disclaimer, the term of this patent is extended or adjusted under 35 U.S.C. 154(b) by 953 days.

(21) Appl. No.: 15/294,299

(22) Filed: Oct. 14, 2016

Related U.S. Application Data (60) Provisional application No. 62/241,148, filed on Oct. 14, 2015.

(51) Int. Cl.
| | |
|---|---|
| *A61B 5/05* | (2021.01) |
| *A61B 5/00* | (2006.01) |
| *G06F 19/00* | (2018.01) |
| *A61B 34/10* | (2016.01) |
| *G16H 40/63* | (2018.01) |
| *G16H 50/20* | (2018.01) |
| *G16H 10/60* | (2018.01) |
| *G06N 20/00* | (2019.01) |
| *A61B 5/369* | (2021.01) |

(52) U.S. Cl.
CPC ............ *A61B 5/4094* (2013.01); *A61B 5/369* (2021.01); *A61B 5/4836* (2013.01); *A61B 5/7275* (2013.01); *A61B 34/10* (2016.02); *G06F 19/3481* (2013.01); *G06N 20/00* (2019.01); *G16H 10/60* (2018.01); *G16H 40/63* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 2007/0150025 A1* | 6/2007 | Dilorenzo | A61B 5/0476 607/45 |
| 2014/0094710 A1* | 4/2014 | Sarma | A61B 5/6868 600/544 |
| 2015/0099962 A1* | 4/2015 | Weiss | A61B 5/4094 600/409 |

* cited by examiner

*Primary Examiner* — Joel F Brutus
(74) *Attorney, Agent, or Firm* — Shook, Hardy & Bacon, L.L.P.

(57) ABSTRACT

Systems, methods and computer-readable media are provided for identifying persons who are likely to benefit from a neurosurgical procedure, such as lobectomy, hemispherectomy, lesionectomy, callosotomy, and the like. Measured values of physiological variables may be combined via a multi-variable predictive model. In some embodiments, this may take the form of a multinomial logistic regression classifier. In other embodiments, the evidence-combining may be implemented via a neural network or support vector machine or similar machine learning or classification methods. In an embodiment, a leading indicator of near-term responsiveness to the regimen may be provided to a caregiver, such as a neurologist, and further may be integrated with case-management software and an electronic health record decision-support system.

20 Claims, 9 Drawing Sheets

```
###########################################################################

#   Epilepsy candidacy multinomial logistic regression for post-op Engel class
outcome

##################################################################### library(statmod)
library(mixcat)
# library(epicalc)

# load data N=437 (329 of 437 cases received surgery) with 2-week, 1-year, and
3-year post-op follow-up for Engel class of seizure reduction
surg <- read.csv(file="c:/0_cerdsm/IP/epilepsy_surgery_candidacy/
dsm_sz_surg3.csv", header=TRUE,
    colClasses=rep("numeric",7))
attach(surg)

# perform multinomial logistic regression with empirical Bayes estimation of
non-parametric distributions
fit1 <- npmlt(engel4 ~ trt + log(yr), formula.npo=~trt, random=~1 + trt, id=id,
k=2, link="clogit", EB=TRUE, maxit=1000)
summary(fit1)

# Coefficients:
Estimate    Std. Error
#     (Intercept) 1     -9.2545        0.7021
#     (Intercept) 2     -7.1390        0.5859
#     (Intercept) 3     -3.6382        0.5520
#     trt 1              9.1152        0.7287
#     trt 2              9.5664        0.7284
#     trt 3              7.0559        1.6293
#     log(yr)            2.0284        0.1548

# Estimated Multivariate NP Dist.:

# Mass Points:
(Intercept)     trt     Std. Error (Intercept)   Std. Error trt
#     mass point 1      -7.8030     5.7305           0.9143                 0.6386
#     mass point 2       3.7271    -2.7372           0.5837                 0.4209

# Masses:
Estimate    Std. Error
#     mass 1     0.32325      0.04978
#     mass 2     0.67675      0.04978

# Random effects mean: all dimensions constrained to 0

# Random effects covariance (lower) and correlation (upper) matrices:

                                    .
                                    .
                                    .
                    CONTINUES IN FIG. 4B
```

FIG. 4A

CONTINUES FROM FIG. 4A

.
.
.

```
# OR = 59.3
# Fisher chi-sq p-value = 3e-16
#                    (Intercept)        trt
#    (Intercept)        29.08         -1.00
#    trt               -21.36         15.69

#                                          (Intercept)        trt
#    Std. Errors of random effects variances:    4.575         2.238

#  -2(Log-Likelihood) : 1579
# Number of iterations : 85
# collapse 4-level Engel classes to 3-levels (4=>3, 2||3=>2, 1=>1)
fit2 <- npmlt(engel3 ~ trt + log(yr), formula.npo=~trt, random=~1 + trt, id=id,
k=2, link="clogit", EB=TRUE, maxit=1000)
summary(fit2)

# Coefficients:
Estimate    Std. Error
#    (Intercept) 1    -9.1962      0.7411
#    (Intercept) 2    -3.2834      0.5777
#    trt 1             9.5504      0.7873
#    trt 2             6.9106      0.8788
#    log(yr)           2.1394      0.1493

# Estimated Multivariate NP Dist.:

# Mass Points:
(Intercept)     trt     Std. Error (Intercept)   Std. Error trt
#    mass point 1    -8.3312     6.1704           0.5996                0.4621
#    mass point 2     3.4856    -2.5816           0.6066                0.4585

# Masses:
Estimate    Std. Error
#    mass 1   0.29497      0.04871
#    mass 2   0.70503      0.04871

# Random effects mean: all dimensions constrained to 0

# Random effects covariance (lower) and correlation (upper) matrices:

#                   (Intercept)     trt
#    (Intercept)       29.04      -1.00
#    trt              -21.51      15.93

#                                          (Intercept)        trt
#    Std. Errors of random effects variances:    3.681         2.221

```

.
.
.

CONTINUES IN FIG. 4C

FIG. 4B

CONTINUES FROM FIG. 4B
.
.
.

```
#   -2(Log-Likelihood) : 1216
# Number of iterations : 67
# compare two fits with Likelihood Ratio Test
# lrtest(fit1, fit2) requires class 'glm'
df1 <- length(surg$pat) - 1 - 6
df2 <- length(surg$pat) - 1 - 4
2*dchisq(abs(fit1$m2LogL - fit2$m2LogL), df=abs(df2 - df1))

# p = 1.6e-79

library(pROC)

# determine ROC AUC
ds4 <- read.csv(file="c:/0_cerdsm/IP/epilepsy_surgery_candidacy/roc.csv")
roc1 <- roc(ds4[,1] ~ ds4[,2], percent=TRUE,
# arguments for auc
# partial.auc=c(100, 90), partial.auc.correct=TRUE,
#   partial.auc.focus="sens",
# arguments for ci
   ci=TRUE, boot.n=100, ci.alpha=0.9, stratified=FALSE,
# arguments for plot
#   auc.polygon=TRUE, max.auc.polygon=TRUE,
   plot=TRUE, grid=TRUE, print.auc=TRUE, show.thres=TRUE)
sens.ci <- ci.se(roc1, specificities=seq(0, 100, 5))
plot(sens.ci, type="shape", col="lightblue")
plot(sens.ci, type="bars")
# AUC = 88% (83-92)

# calculate significance (column-major)
x2 <- matrix(c(311,18,24,84), nrow=2)
fisher.test(x2, alternative="two.sided")

# sensitivity = 95% (92-97)
# specificity = 78% (74-82)
# prevalence  = 75% (71-79)
# PPV = 93% (90-95)
# NPV = 82% (79-86)
```

FIG. 4C

| Patient... | | | | | | |
|---|---|---|---|---|---|---|
| | | | enter | | | |
| • Positive findings on video EEG (ICD-9 proc 89.19; CPT-4 7055x)? (Y/N) | | | Y | | | |
| • Positive findings on MRI of head (ICD-9 proc 88.91; CPT-4 9595x)? (Y/N) | | | Y | | | |
| • Epileptogenic focus or etiology... | | | 7-Mesial temporal sclerosis | | | |
| • Complete resection possible without unacceptable risk or CC? (Y/N) | | | Y | | | |
| enter an "x" in each applicable cell | | | | | | |
| | Anxiety (300.xx) | Depression (311.xx) | ADHD (314.xx) | Devel delay or cog deficit (315.xx) | Post-procedural CC (V45.89) | Long-term use of AED (V58.69) |
| • Secondary or comorbid conditions include... | x | x | x | | | x |

| evaluate | |
|---|---|
| | results |
| data complete? | Yes |
| Candidate for surgery? | Yes |

| | 12 months | 36 months |
|---|---|---|
| Post-op probability of Engel Class 1 (seizure-free) | 47% | 89% |
| Post-op probability of Engel Class 2 (>90% reduction of seizure frequency) | 45% | 10% |
| Post-op probability of Engel Class 3 (50% to 90% reduction of seizures frequency) | 5% | 1% |
| Post-op probability of Engel Class 4 (unchanged or worse seizure frequency) | 3% | 0% |
| Probability of Engel Class 1 without surgery | 0% | 0% |
| Probability of Engel Class 2 without surgery | 0% | 1% |
| Probability of Engel Class 3 without surgery | 2% | 19% |
| Probability of Engel Class 4 without surgery | 97% | 80% |

FIG. 5A

| pat | id | engel4 | engel3 | trt | yr | surg |
|---|---|---|---|---|---|---|
| 1 | 1103 | 4 | 3 | 1 | 0.04 | 1 |
| 1 | 1103 | 1 | 1 | 1 | 1 | 0 |
| 1 | 1103 | 2 | 1 | 1 | 3 | 0 |
| 2 | 1104 | 4 | 3 | 1 | 0.04 | 1 |
| 2 | 1104 | 2 | 1 | 1 | 1 | 0 |
| 2 | 1104 | 2 | 1 | 1 | 3 | 0 |
| 3 | 1105 | 2 | 2 | 1 | 0.04 | 1 |
| 3 | 1105 | 3 | 1 | 1 | 1 | 0 |
| 3 | 1105 | 3 | 1 | 1 | 3 | 0 |
| 4 | 1106 | 4 | 2 | 1 | 0.04 | 1 |
| 4 | 1106 | 1 | 1 | 1 | 1 | 0 |
| 4 | 1106 | 1 | 1 | 1 | 3 | 0 |
| 5 | 1107 | 4 | 3 | 0 | 0.04 | 0 |
| 5 | 1107 | 4 | 3 | 0 | 1 | 0 |
| 5 | 1107 | 4 | 3 | 0 | 3 | 0 |

FIG. 5B

DETERMINING PATIENT CANDIDACY FOR EPILEPSY NEUROSURGICAL PROCEDURE

CROSS-REFERENCE TO RELATED APPLICATIONS

This application claims the benefit of U.S. Provisional Application No. 62/241,148; entitled "Predicting Candidacy for Epilepsy Neurosurgical Procedure," filed Oct. 14,2015, which is expressly incorporated by reference in its entirety.

BACKGROUND

Epilepsy is a common neurological disorder affecting approximately 50 million people worldwide, and is associated with considerable morbidity and mortality. Epilepsy is defined as a pre-disposition to experience seizures as a result of abnormal (excessive or hyper-synchronous) neuronal activity in the brain. Seizures are classified as partial (focal) or generalized, depending on the extent to which they affect the brain. Only some causes of seizures, however, may be treated surgically. But because of limited objective data regarding the probabilities of surgical outcomes, many good candidates choose not to have surgery either because clinicians are unable to give them a proper risk analysis or because clinicians do not recognized that surgery is a valid option. Thus, there is a need for an objective way to determine whether someone is a candidate for surgical intervention and a way to present objective information upon which the candidate can make a decision as to whether surgery is appropriate.

SUMMARY

Systems, methods and computer-readable media are provided for automatic identification of refractory epileptic patients having features supportive of candidacy for epilepsy surgery. In particular, embodiments of this disclosure are directed to (a) monitoring human patients with epilepsy that has proven refractory to antiepileptic medications, (b) quantitatively determining candidacy for epilepsy surgery and predicting Engel Class severity of seizures at a period of months subsequent to computing the prediction, and (c) informing the care provider clinicians' decisions and communications with the patient as to likely risks and benefits surgical and non-surgical alternatives.

Embodiments of the disclosure are further directed to context-sensitive outcomes prediction, risk stratification, and optimization of the assessment, communication, and decision-making to manage epilepsy refractory to medical treatment in humans, and in an embodiment may take the form of a platform for embedded decision support in an electronic health record (EHR) system. An aim of some embodiments relates to automatically identifying persons who are suitable candidates for surgery through the use of electroencephalogram and magnetic resonance imaging measurements and a system and method for signal-processing that calculate multinomial post-operative outcomes probabilities for patients possessing features similar to those of the present patient. Additionally, in some embodiments the indicator may provide notice of the effectiveness (or lack thereof) of alternative therapeutic regimens and assist in further decision-making in the medical management of the patient. Still another aspect of some embodiments concerns the combining of the evidence via a multi-variable predictive model, such as a multinomial logistic regression equation to form a quantitative probability of medical and surgical outcomes materializing within a subsequent time interval, and the rendering of the predicted probability to one or more human decision-makers in the context of an electronic health record information system.

BRIEF DESCRIPTION OF THE DRAWINGS

Embodiments of the invention are described in detail below with reference to the attached drawing figures, wherein.

DETAILED DESCRIPTION

The subject matter of the invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Accordingly, at a high level, this disclosure describes, among other things, methods and systems, for automatically identifying persons who are likely to benefit from a neurosurgical procedure, such as lobectomy, hemispherectomy, lesionectomy, callosotomy, and the like. In embodiments described herein, measured values of physiological variables are combined via a multi-variable mathematical model. In some embodiments, this may take the form of a multinomial logistic regression equation. In other embodiments, the evidence-combining may be implemented via a neural network or support vector machine or other methods such as are known to those practiced in the art. In all such embodiments, the present invention provides a leading indicator of near-term responsiveness to the regimen. In one exemplary embodiment, the device is integrated with case-management software and electronic health record decision-support system.

By way of example and not limitation, a user using an embodiment of the invention may be able to more confidently decide as to the giving or withholding of neurosurgery for epilepsy, or other interventions. In this exemplary embodiment, the computer system may include an app which when executed receives user data from the device, calculates a plurality of EEG and MRI test measures, combines these in a mathematical model, and communicates the composite results to the clinician user, case-management software, decision-support systems, or electronic health record systems. For example, the system may notify the user in advance, via a notification message or electronic mail, and may also notify the user's health plan, electronic-health record decision-support systems or personal health record systems, via a call, HTTP, SMS text-message, or other form of electronic or radiofrequency communication, that the user may be likely to benefit from a disease-modifying medication regimen. This enables the care providers to take appropriate measures, including determining insurance coverage for the regimen or other aspects.

As described above, epilepsy is a common neurological disorder affecting approximately 50 million people worldwide, and is associated with considerable morbidity and mortality. More than 50% of patients are diagnosed with 'idiopathic' epilepsy (cases where an anatomical structural cause cannot be found on EEG or MRI or other studies). The balance of patients have epilepsy that is associated with structural abnormalities in the brain, such as embryodysplastic tissue abnormalities, tumor, stroke, head injury, or infection. These definitions are undergoing a significant review in the light of new concepts that have emerged from recent research, such as that of "network epilepsy", which has challenged the traditional dichotomy between partial (focal) and generalized epilepsy.

Antiepileptic drugs (AEDs) remain the mainstay of treatment for epilepsy. Seizure freedom is achieved in approximately 50% of patients with the pharmacotherapy. The success rate increases with second or third add-on medications. Unfortunately, AEDs can have suboptimal tolerability profiles, especially with regard to behavioral and cognitive aspects. When a patient fails to respond to adequate trials of two AEDs because of poor efficacy and/or tolerability, a diagnosis of "treatment-resistant" or "refractory" epilepsy is formulated.

In general, the cognitive effects of anti-epileptic drugs (AEDs) are less than the sum total of other factors, but because AEDs are the major therapeutic modality for epilepsy, they are of special concern. AED-induced cognitive side effects are increased with rapid initiation, higher dosages, and polytherapy.

Differential cognitive effects can be seen (e.g., worse performance on phenobarbital), but the magnitude of cognitive effects is relatively modest effects for most AEDs. However, even this modest effect can be clinically significant and impact the patient's quality of life. In addition, some patient groups may be at particular risk (e.g., elderly, children, fetus). The ultimate therapeutic goal is to control seizures with no or minimal side effects.

The cognitive side-effects profile of an AED is just one factor in the selection of therapeutic options. Ongoing seizures can be detrimental to both cognition and quality of life. Patients who are refractory or intolerant to AED therapy should be referred for video EEG monitoring to determine if the patient is a candidate for epilepsy surgery.

Approximately 30% of all epileptic patients are not satisfactorily controlled by available antiepileptic drugs. In such cases, other treatments are available, including novel AEDs, ketogenic diet, surgery to resect the epileptogenic tissue in the brain, and more recently, implantable neurostimulation devices. The adverse seizure and neurobehavioral prognosis in patients with these disorders provides the justification to search for innovative treatments. These include moderately invasive treatments such as vagus nerve stimulation (VNS), responsive neural stimulation (RNS) that detects the onset of new seizure activity and delivers impulses specifically to the region in the brain where it is originating, and deep brain stimulation (DBS).

A significant percentage of these patients have epileptic syndromes which could potentially be treated by resective surgery. Today, many patients who were once considered inoperable are candidates for a wide variety of surgical procedures. This trend is particularly striking at pediatric centers that serve patients with diverse forms of epilepsy that can severely compromise children's developmental milestones. Several resective neurosurgical procedures are available to help these patients, including frontal and temporal lobectomy, lesionectomy, sub-pial transection, hemispherectomy, and callosotomy.

Evaluation for candidacy for these procedures may include: characteristics of the seizures; localization of the epileptogenic focus/foci; psychosocial factors; surgical risks; and weighing these factors against the risks of continued, uncontrolled epilepsy.

Embodiments of the present disclosure aim to determine which patients are acceptable candidates to receive a resective surgical procedure and, among these, determine which ones are statistically likely to achieve significant abatement of seizure frequency as a beneficial result of the procedure. Those at risk of a high frequency of residual seizures or a postoperative memory or cognitive deficits can be identified via multivariate models that utilize noninvasive measures of cerebral function and structure, together with demographic and clinical variables.

Newer diagnostic techniques, including structural and functional imaging, EEG monitoring, and intraoperative electrocorticography and other surgical technology, can provide a decisive representation of the etiology and expression of the epileptic focus, including accurate cortical localization. Functional MRI is being used in some centers to lateralize and localize language function in epilepsy surgery candidates as an alternative to the traditional Wada test.

However, the sophisticated tools for preoperative evaluation and an expanding knowledge base have not thus far resulted in dramatic changes in the utilization of epilepsy surgery. Decision-support tools and accurate predictive models are needed to more clearly identify surgical candidates and to quantitatively characterize the likely comparative benefits of alternative therapies, to properly inform the patients' and the clinicians' decision-making In other words, the technological advances applied to diagnostic and therapeutic methods have improved the process and accuracy with which epileptic patients who may benefit from surgery may be identified, but subjective determinations of candidacy are highly variable and are not accompanied by context-specific guidance as to comparative outcomes or benefits. Up to 80% of the patients with focal epilepsies symptomatic of well-defined lesions may become free of seizures after excision of the lesion or epileptogenic focus. Other forms of epilepsy, such as the so-called catastrophic infantile forms, may improve temporarily when techniques such as hemispherectomy or callosotomy are used. The morbidity associated with these surgical procedures is minimal, while, by contrast, the morbidity of remaining on multiple AEDs is considerable.

Objective, systematic evaluation of the patients is preferable, with the collaboration of neurologists, neuropsychologists, neurophysiologists, neuroimaging specialists, psychiatrists and neurosurgeons. From such evaluation clear answers to two key questions are sought: (1) Is the present patient is a good surgical candidate or not? and (2) What are the chances that a desirable reduction in seizure frequency can be achieved with the proposed surgical procedure, compared to other therapeutic alternatives?

Candidate selection has been facilitated by observational information bearing on the natural history of medically refractory seizures and the greater-than-expected incidence of early hippocampal sclerosis. Because the majority of children suffer from extra-temporal epilepsy, ictal single photon emission computed tomography (SPECT) and subdural electroencephalogram (EEG) recording are increasingly important for both seizure and functional localization, and have been shown to be well tolerated, even in very young patients. Furthermore, the outcome of both excisional and commissural procedures in children with respect to seizure control is similar to that reported for adults, irrespective of age.

Epilepsy surgery can result in complete seizure remission rates of up to 80% in patients with mesial temporal sclerosis and unilateral seizures. The seizure-free rate after surgery for patients with extra-temporal non-lesional epilepsy has ranged between 30% and 40%. Seizure-free rates following temporal lobectomy or hemispherectomy are consistently 65% to 70% in adults and 68% to 78% in children. Extra-temporal resections less commonly lead to a seizure-free outcome, although one recent childhood series reported a seizure-free rate of 62% following extra-temporal epilepsy surgery. With both temporal and extra-temporal resections, most patients have a reduction in seizures following surgery but are not completely seizure free.

One study indicated that there is a strong tendency for patients with severe pathologic features to have MRI abnormalities and favorable surgical outcome associated with complete surgical resection. By contrast, patients with incomplete resection, mild pathologic features, or the presence of secondary tonic-clonic seizures have a high chance of a poorer surgical outcome.

Hemispherotomy in patients with intractable epilepsy is generally reserved for individuals with unilateral epileptiform abnormalities or lesions on MR imaging. In some published studies, a substantial percentage of patients with bilateral foci benefited from surgery the despite bilateral seizure onset.

In lesional temporal lobe epilepsy excluding hippocampal sclerosis, the extent of resection and the histology are the key prognostic factors for seizure frequency reduction outcome. Epilepsy-associated low-grade tumors (gangliogliomas (GG) and dysembryoplastic neuroepithelial tumors (DNT)), cavernomatous malformations (CM) or focal cortical dysplasia (FCD) are the main pathological entities in such cases. Intrinsic epilepsy associated tumors may have diffuse borders and may be located adjacent to temporal speech areas, CM or FCD may have contact to deep structures like speech or visual tracts. Thus, intraoperative imaging and neuronavigation may guide the extent of surgical resection so as to avoid postoperative neurological deterioration and balance seizure-reduction benefits against risks and functional losses.

In cases where complete resection is not practical or where the epileptogenic foci are diffuse or bilateral, it may not be possible to entirely discontinue AED medications post-operatively. However, in most such cases a significant improvement in Engel Class can be achieved, and a decrease in the number of prescribed AEDs or a reduction of their dosages is possible. Combined, these results constitute a balance of benefits that outweighs the risks and costs associated with neurosurgery. Currently, conventional methods fail to forecast context-specific outcomes. For example, it underpredicts efficacy in temporal lobe seizures, underpredicts efficacy in bilateral foci, and neglects spontaneous abatement/remission in pediatric epilepsies. Embodiments are presented below that overcome many of these problems and more, which currently exist with conventional methods.

With regard to some embodiments described herein of a method of calculating future outcomes probabilities of both surgical and medical treatment alternatives, one disadvantage of separately estimating by logistic regression the different levels of the dependent (outcome) variable of seizure frequency or Engel Class is that statistical measures of goodness-of-fit are not applicable. One cannot simply sum the separate regressions' deviances or the log-likelihoods of the separate models to get an overall measure of goodness-of-fit for the predictions. Therefore, some embodiments perform multinomial logistic regression to simultaneously optimize the fitting of the independent input-variables data to the multi-level dependent outcome variable.

In light of the foregoing, an improved predictive method and system has been devised according to embodiments of the invention described herein. In some embodiments, a prediction classification or decision-support alert signal is emitted or provided at logistically convenient times with respect to decision-making by Neurologists and Neurosurgeons. Some embodiments entail the use of commonly-available EEG and MRI tests. The timely determining of 12- and 36-month predicted post-operative outcomes is performed in such a manner so as not to be unduly dependent on scarce or expensive resources.

Figure 1A:
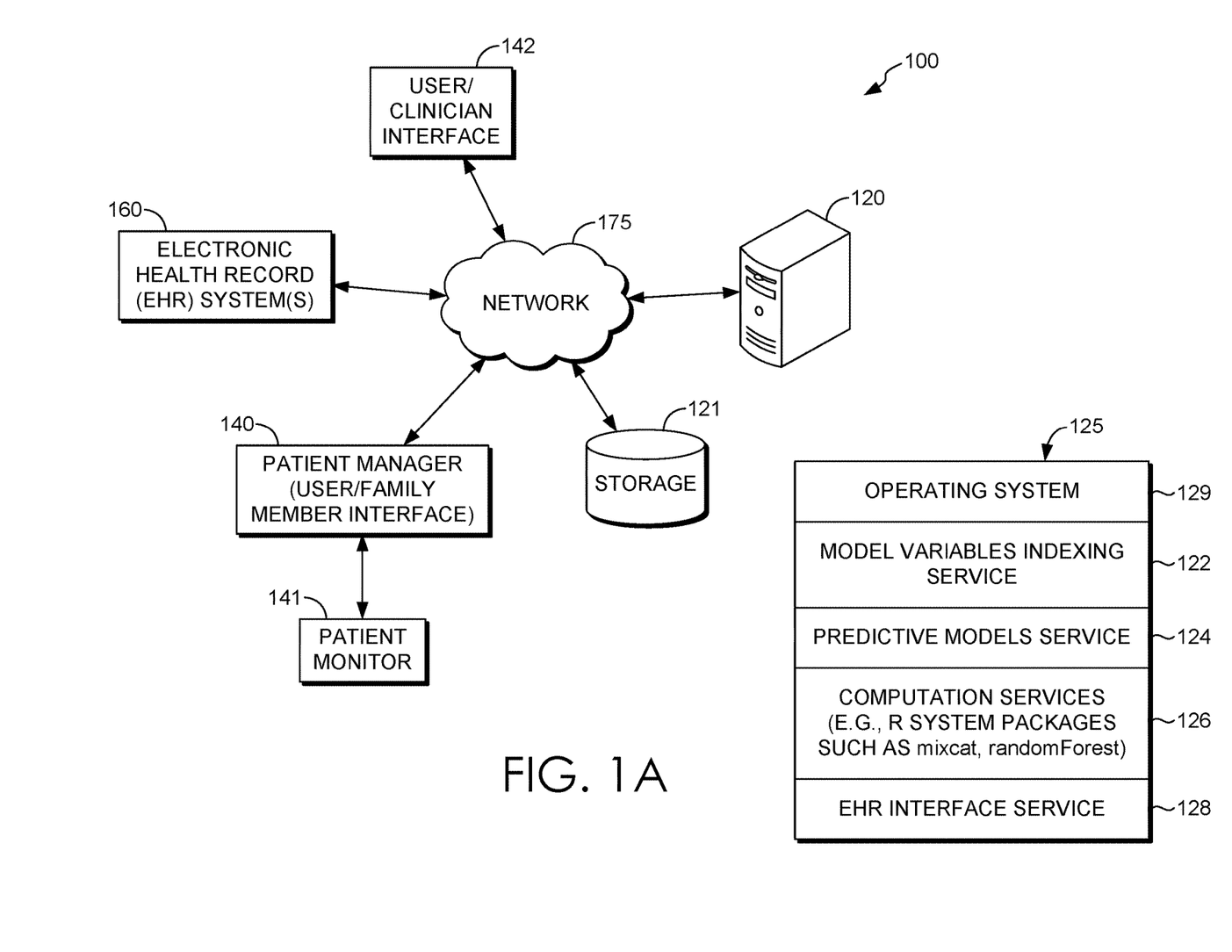
FIGS. 1A and 1B depict aspects of an illustrative operating environment suitable for practicing an embodiment of the disclosure.

Referring now to the drawings in general, and initially to FIG. 1A in particular, an aspect of an operating environment 100 is provided suitable for practicing an embodiment of the invention. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, example operating environment 100 provides an aspect of a computerized system for compiling and/or running embodiments of identifying persons who are likely to benefit from a neurosurgical procedure. Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or a plurality of EHR systems such as hospital EHR systems, health information exchange EHR systems, ambulatory clinic EHR systems, EEG or Electrophysiology systems, psychiatry/neurology EHR systems, MRI diagnostic imaging or PACS system, and may be implemented in computer system 120. Similarly, EHR system 160 may perform functions for two or more of the EHR systems (not shown).

Network 175 may comprise the Internet, and/or one or more public networks, private networks, other communications networks such as a cellular network, or similar network (s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system 160 include one or more data stores of health records, which may be stored on storage 121, and may further include one or more computers or servers that facilitate the storing and retrieval of the health records. In an embodiment, the health records comprise a personal health record for a user or patient. In some embodiments, EHR system 160 may be implemented as a cloud-based platform or may be distributed across multiple physical locations. EHR system 160 may further include record systems, which store real-time or near real-time patient (or user) information, such as patient monitor 141, which may comprise one or more wearable, bedside, or in-home patient monitor(s), for example.

Example operating environment 100 further includes provider user/clinician interface 142 communicatively coupled through network 175 to an EHR system 160. Although environment 100 depicts an indirect communicative coupling between interface 142 and EHR system 160 through network 175, it is contemplated that an embodiment of interface 142 is communicatively coupled to EHR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A provider clinician application facilitates accessing and receiving information from a user or health care provider about a specific patient or set of patients. Embodiments of interface 142 also facilitates accessing and receiving information from a user or health care provider about a specific patient or population of patients including patient history; health care resource data; variables measurements, time series, and predictions (including plotting or displaying the determined outcome and/ or issuing an alert) described herein; or other health-related information, and facilitates the display of results, recommendations, or orders, for example. In an embodiment, interface 142 also facilitates receiving orders for the patient from the clinician/user, based on the results of monitoring and predictions. In some embodiments, interface 142 may also be used to display patient hydration status, forecast, or related information. Interface 142 may also be used for providing diagnostic services or evaluation of the performance of various embodiments.

Example operating environment 100 further includes computer system 120, which may take the form of a server, which is communicatively coupled through network 175 to EHR system(s) 160 storage 121, and user manager 140.

Embodiments of user manager 140 may take the form of a user interface and application, which may be embodied as a software application operating on one or more mobile computing devices, tablets, smart-phones, front-end terminals in communication with back-end computing systems, laptops or other computing devices. In some embodiments, manager 140 includes a Web-based application or set of applications that is usable to manage user services provided by embodiments of the invention. For example, in some embodiments, manager 140 facilitates processing, interpreting, accessing, storing, retrieving, and communicating information acquired from monitor 141. Moreover, in some embodiments of manager 140, an interface component may be used to facilitate access by a user to functions or information on monitor 141, such as operational settings or parameters, user identification, user data stored on monitor 141, and diagnostic services or firmware updates for monitor 141, for example.

As shown in example environment 100, manager 140 is communicatively coupled to monitor 141 and to network 175. Embodiments of monitor 141 comprise one or more sensor components operable to acquiring physiologic information, which may include neurologic, biometric, or other sensible information about a user and which may be acquired as needed, periodically, or as one or more timeseries. In some embodiments, monitor 141 comprises an MRI, EEG, or one or more sensor components operable for sensing neurological data of a patient. In some embodiments, monitor 141 comprises a sensor operable to sensea skin conductance or galvanometry or impedance. In some embodiments, one or more sensor components of monitor 141 may comprise a user-wearable sensor component or sensor component integrated into the user's or patient's living environment. Examples of sensor components of monitor 141 include wherein the sensor is positioned on or near the user's head, attached to the user's clothing, worn around the user's head, neck, leg, arm, wrist, ankle, etc., skin-patch sensor, ingestible or sub-dermal sensor, or wherein sensor component(s) are integrated into the user's living environment (including the bed, pillow, bathroom, hospital room, etc.), sensors operable with or through a smart phone carried by the user, for example.

Embodiments of monitor 141 may store user-derived data locally or communicate data over network 175 to be stored remotely. In some embodiments, manager 140 is wirelessly communicatively coupled to monitor 141. Manager 140 may also be embodied as a software application or app operating on a user's mobile device. In some embodiments, manager 140 and monitor 141 are functional components of the same device, such as a device comprising a sensor and a user interface. In some embodiments, manager 140 is embodied as a base station, which may also include functionality for charging monitor 141 or downloading information from monitor 141.

Computing system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on monitor 141 or manager 140 for performing signal conditioning of the measured patient variable(s). In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 140 and 142. In some embodiments, interface 142 operates in conjunction with software stack 125.

In embodiments, model variables indexing service 122 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126. Predictive models service 124 in general is responsible for providing models for predicting candidacy for surgery, such as described in connection to method 200 of FIG. 2.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including for example, mixcat (missed effects cumulative link and logistic regression models) and Random Forest (for performing classification and regression) packages, or similar services.

Figure 4A:
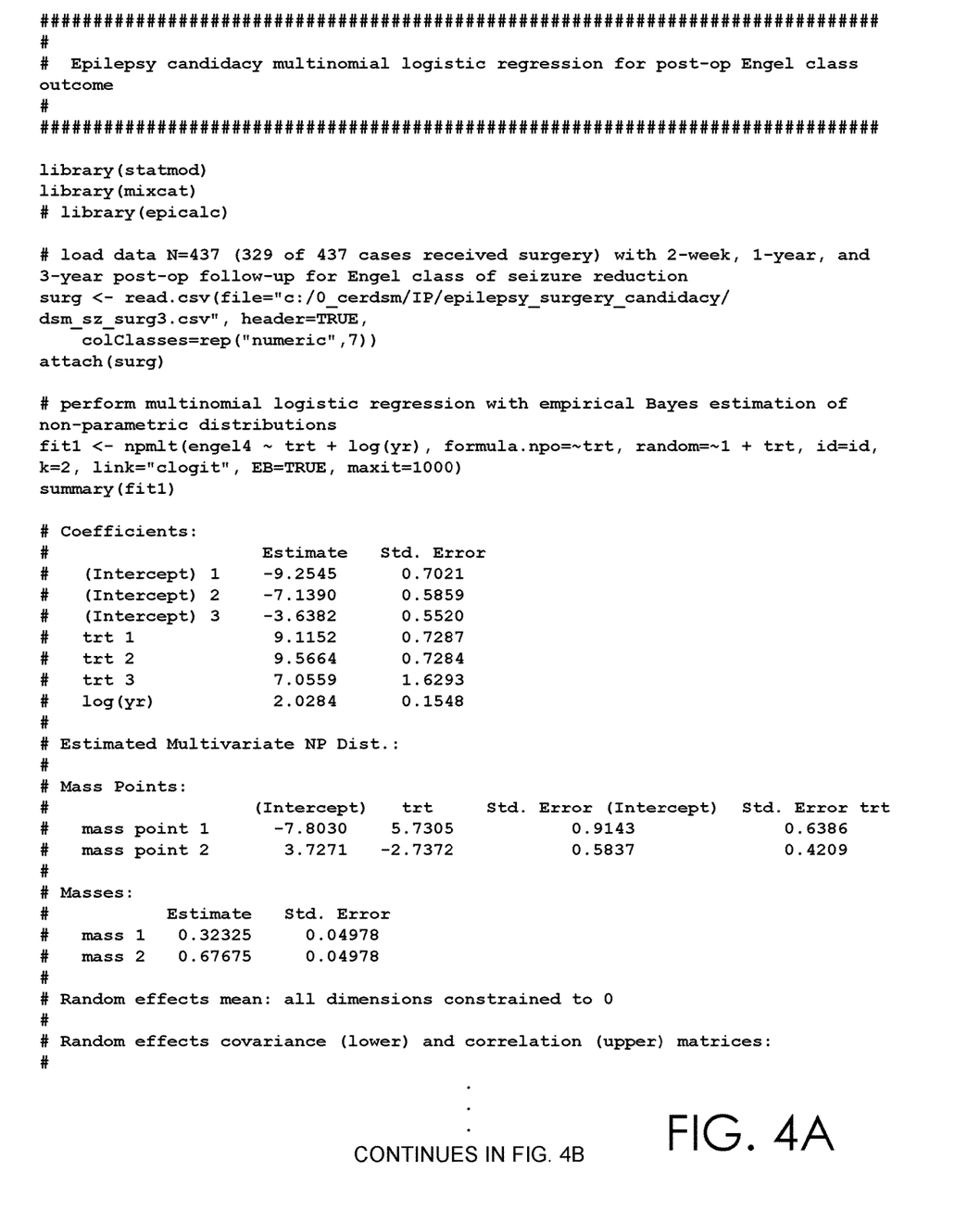
FIGS. 4A-4C illustratively provide example embodiments of a computer program routine used for implementing an embodiment of the disclosure.
Figure 4B:
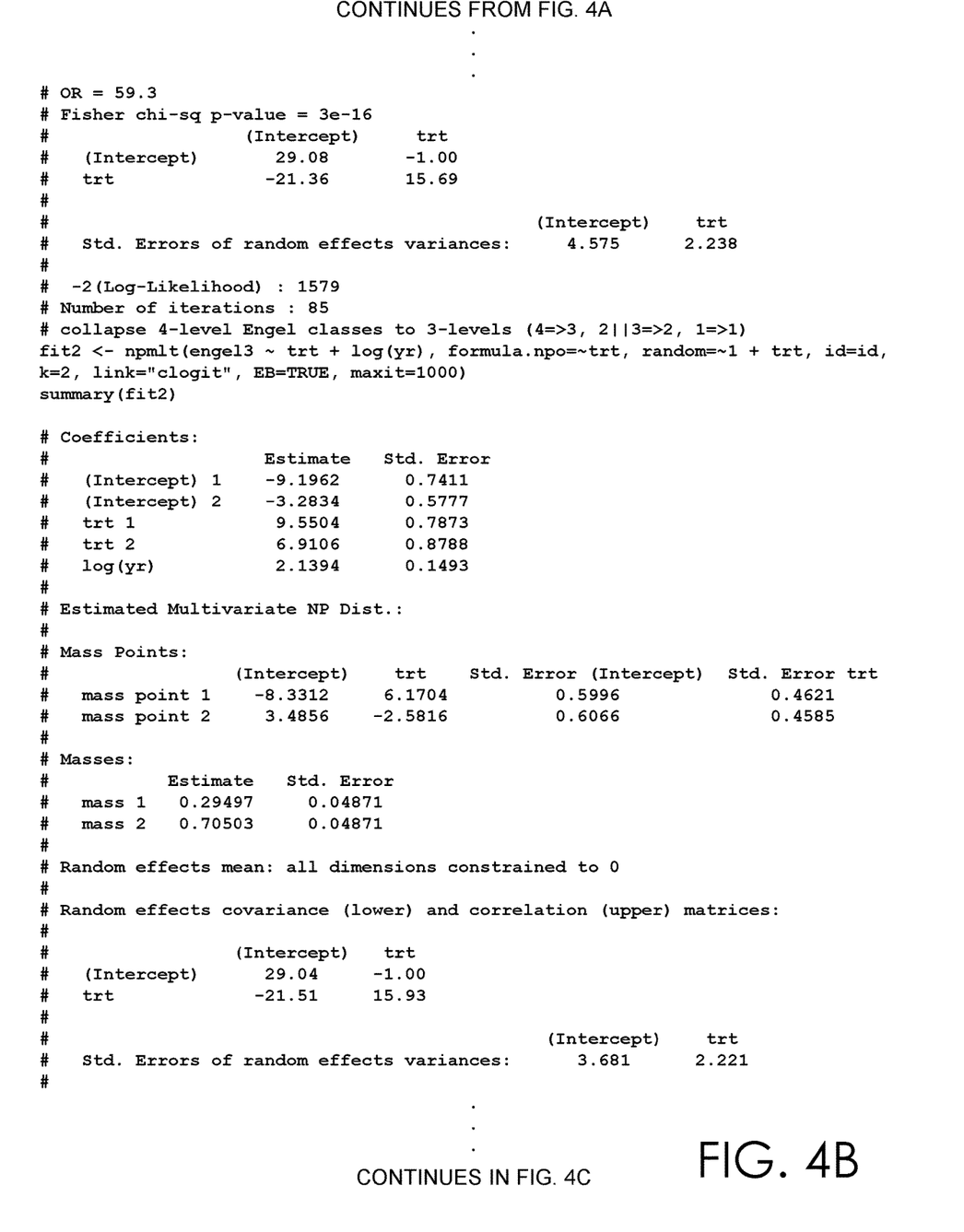
Figure 4C:
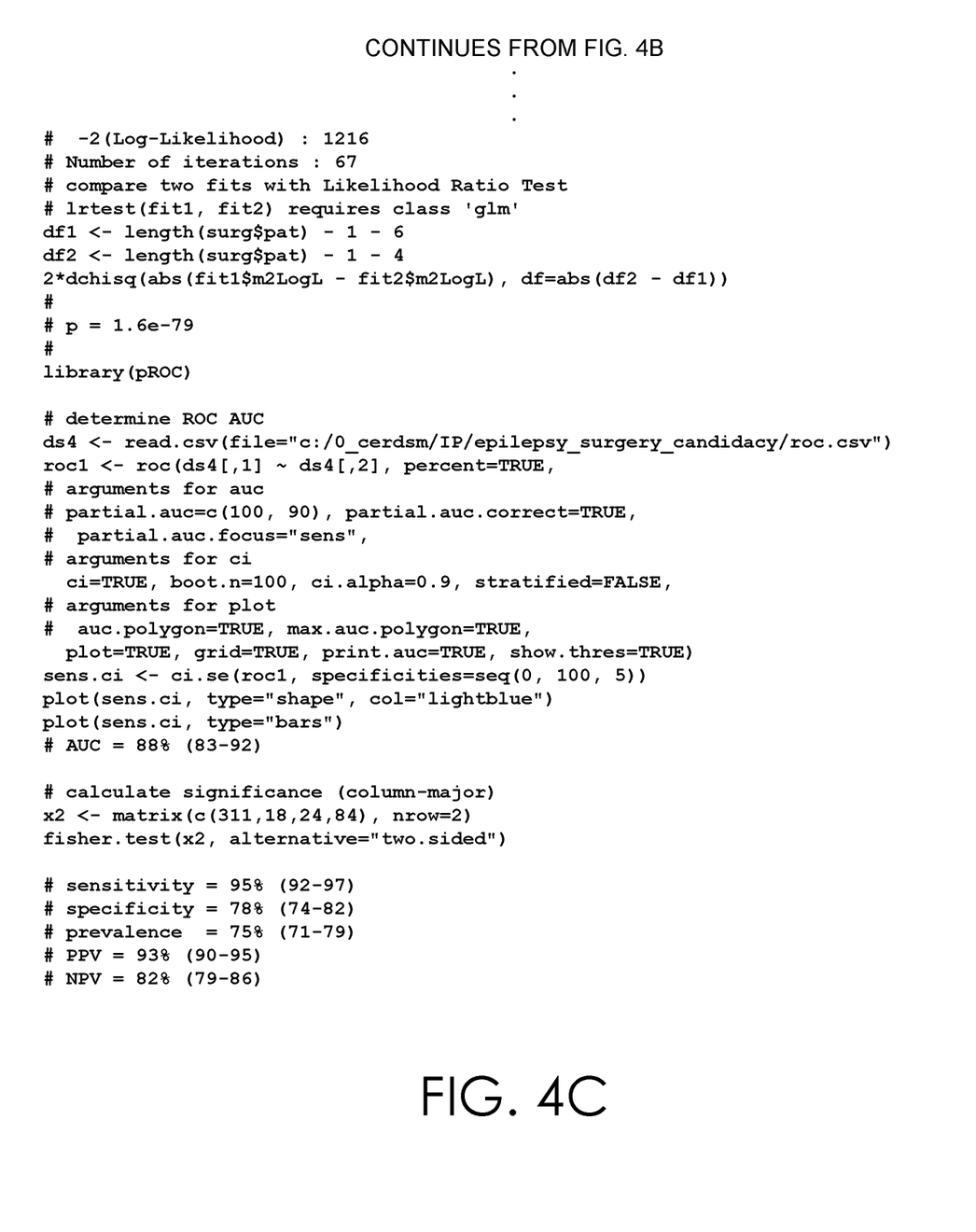

In an embodiment, computation services 126 include the services or routines, which may be embodied as one or more software agents or routines such as the example embodiments of computer program routines illustratively provided in FIGS. 4A-4C. In some embodiments, computation services 126 use EHR system interface services 128, or lab information, or monitor 141 information (such as from a patient-worn sensor) provided by a stream processing service (not shown). Some embodiments of stack 125 may further use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
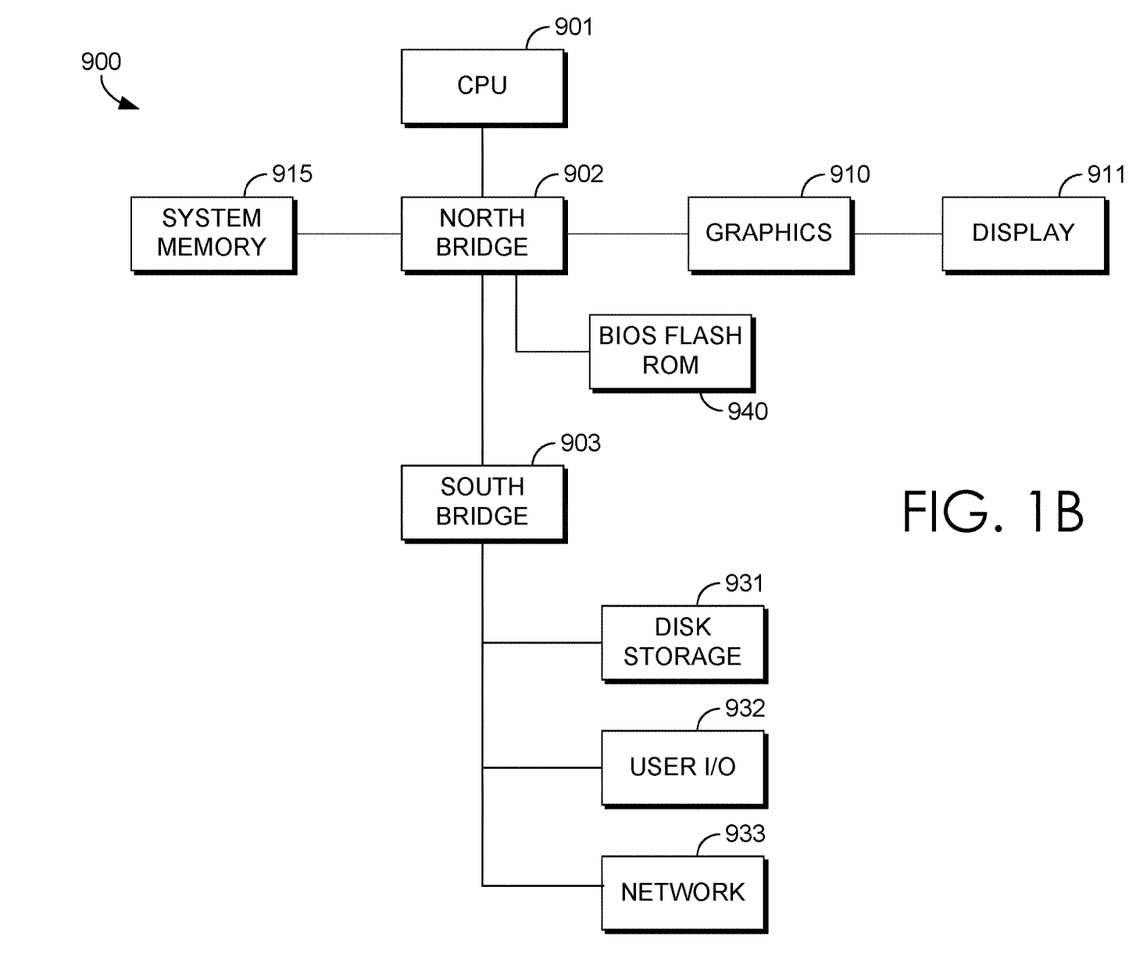

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
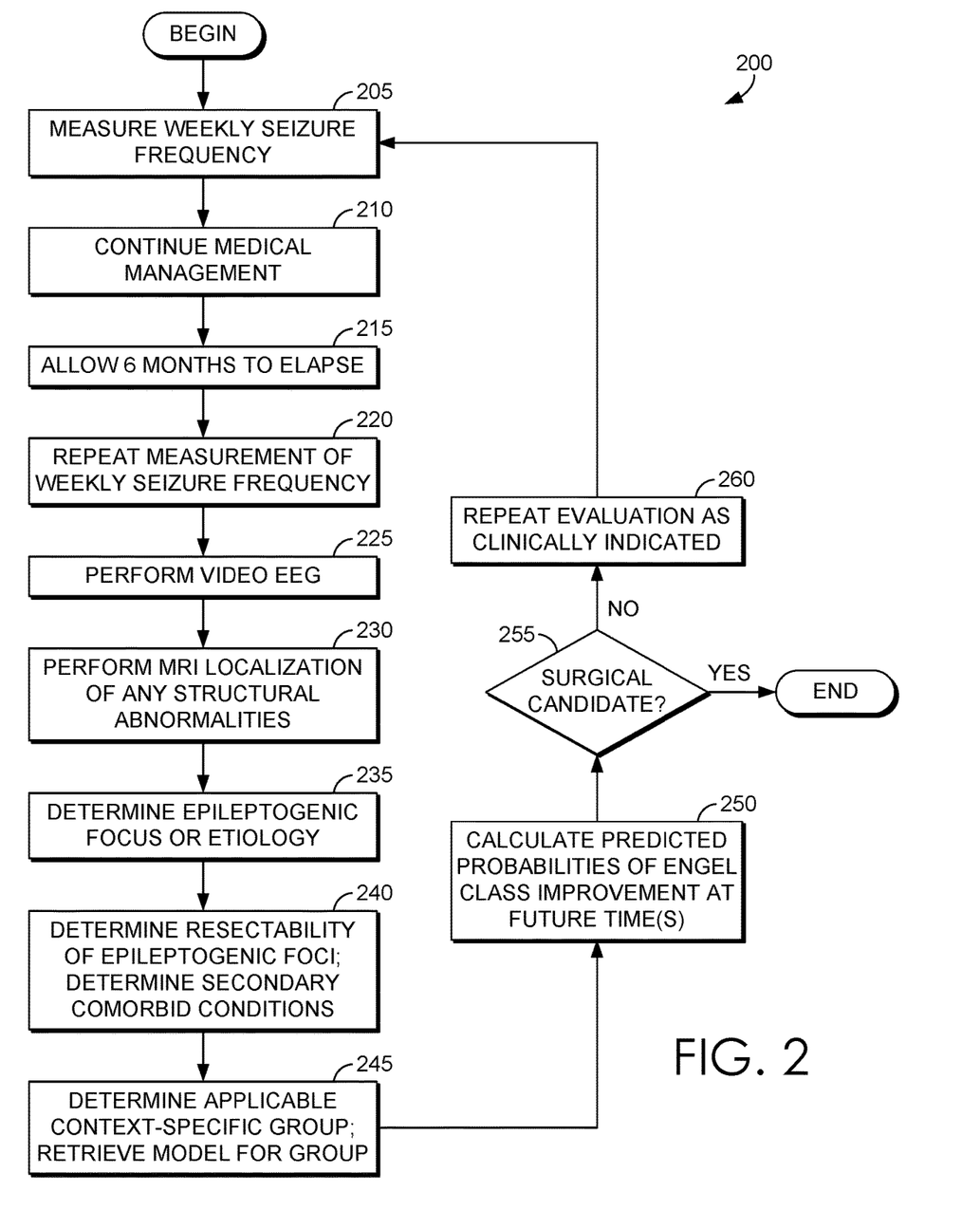
FIG. 2 depicts a flow diagram of a method for predicting epilepsy surgery candidacy in an individual, in accordance with an embodiment of the disclosure.
Figure 5A:
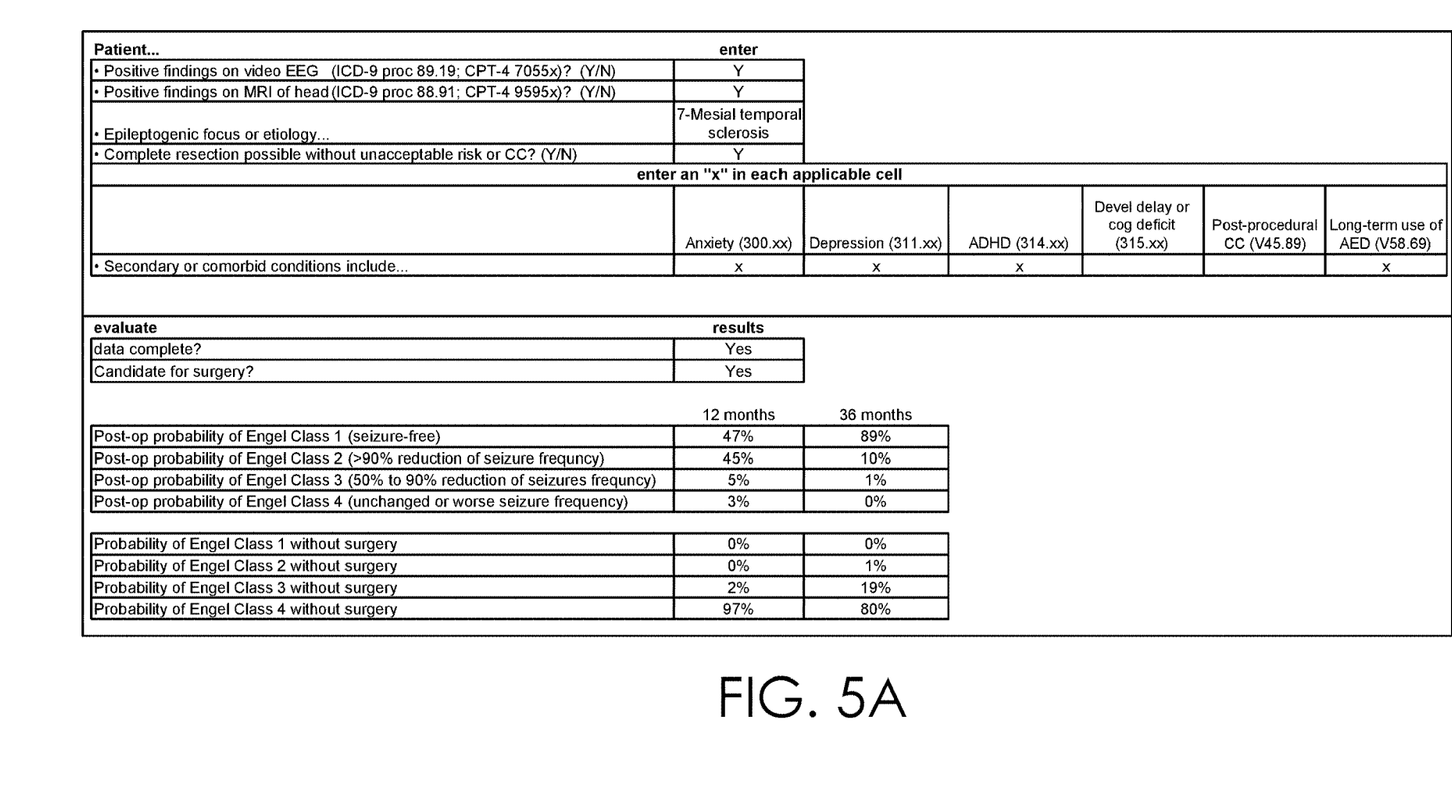
FIG. 5A depicts one example of a user interface for a surgery candidacy predictive model, in accordance with an embodiment of the disclosure.
Figure 5B:
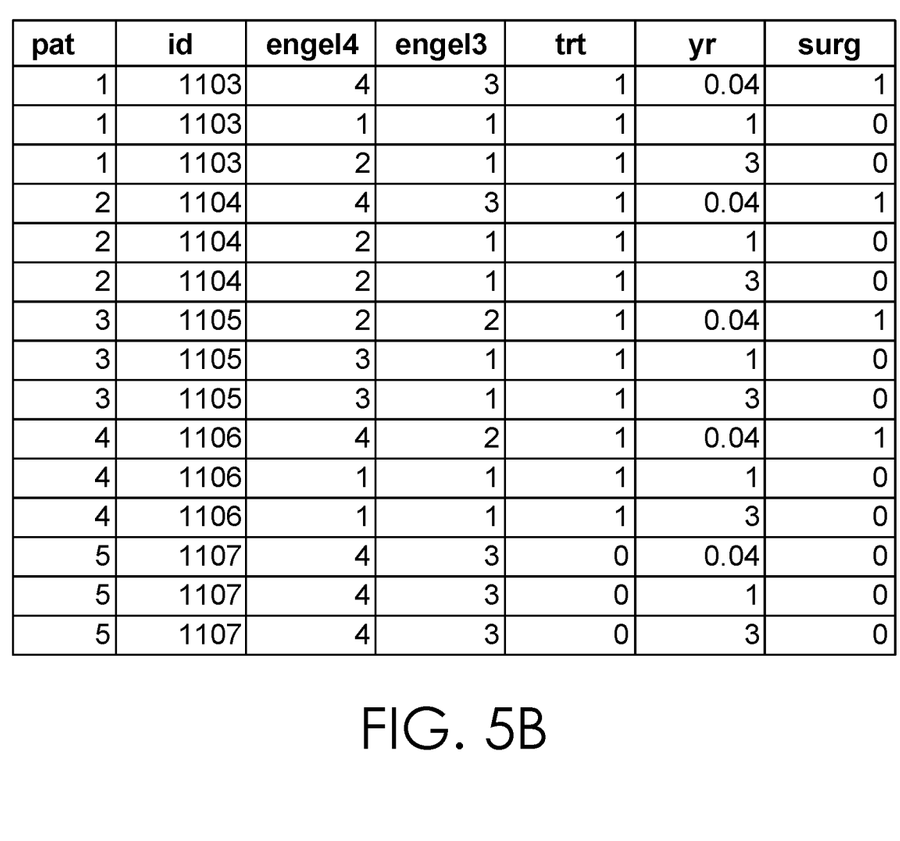
FIG. 5B depicts patient data and analysis associated with the model of FIG. 5A.

Turning now to FIG. 2, a flow diagram is provided of a method 200 for determining a patient who is a candidate for epilepsy surgery. In particular, example method 200 comprises a process for predicting epilepsy surgery candidacy in an individual, where the features are of a type and severity as are associated with particular clinical contexts or groupings. Steps 205 through 220 seizure frequency is determined over a period of time, such as 3 months, 6 months, or a year, for example. In some embodiments, the period of time may be set by a third party, such as an insurance payor, and is not limited to the 3 months, 6 months, or one year examples. As shown in example method 200, at step 205, seizure frequency is measured. In one embodiment, it is measured weekly. Alternatively it may be measured monthly or in some instances, daily. In some embodiments, a user interface such as shown in FIG. 5A is used to facilitate the measurement. At step 210, medical management for the patient continues (or resumes). At step 215, a period of time, such as 6 months, is allowed to elapse before (at step 220) repeating the measurement of seizure frequency.

At step 225 and 230, EEG and/or MRI localization of any structural abnormalities is performed on the patient. At step 235, epileptogenic focus or etiology is determined. Some embodiments of step 235 may determine the epileptogenic focus or etiology based on a text report from each of the exams, such as the EEG and MRI. Further, it should be understood that, according to some embodiments, future exams may be developed that further determine structural abnormalities. For instance, it is foreseen that these developments may also be used at steps 225 and 230 in combination with or in lieu of the EEG or MRI.

At step 240, the resectability of epileptogenic foci and secondary comorbid conditions are determined. In some embodiments, the resectability may generally be determined by a computer-performed decision-support system, by one or more surgical clinicians, or a combination of both. If it is determined not to be resectable at step 240 without an unacceptable risk, the patient may not be a candidate for surgery. Examples of epileptogenic focus or etiology include, but are not limited to, malignant neoplasm of the brain, hamartoma or other benign neoplasm of the brain, endocrine or neuroendocrine neoplasm in the brain, neoplasm of uncertain behavior in the brain, history of neoplasm in the brain, anomaly of cerebrovascular system, or mesial temporal sclerosis. Secondary comorbid examples include; anxiety, depression, ADHD, developmental delay or cognitive deficit, post-procedural complications from other procedures, long term use of AEDs, or the like. Each of the examples of epileptogenic focus and secondary comorbid conditions was found to be statistically significant with respect to the final probability outcome.

At step 245, an applicable context-specific group is determined for the patient based on the information described herein, and a classification model retrieved for that group. In some embodiments, the models use logistic regression and may be particular to one of the context-specific groups. In some embodiments, models may use other classification means, such as Bayesian aggregation, random forest, neural network, support vector machine, or other statistical classification processes. Examples of context-specific groups may include, without limitation: 1—Malignant neoplasm of the brain; 2—Hamartoma or other benign neoplasm of the brain; 3—Endocrine or neuroendocrine neoplasm in the brain; 4—Neoplasm of uncertain behavior in the brain; 5—History of neoplasm of the brain; 6—Anomaly of cerebrovascular system; 7—Mesial temporal sclerosis; or the like. At step 250, predicted probabilities of Engel Class improvement at future time(s) are calculated. Improvement probabilities may include the probability of improvement with surgery and the probability of improvement without surgery. In some embodiments, computer program routines, such as illustratively provided in FIGS. 4A-4C are used in step 250. In one embodiment, the results of step 250 may be provided to a user/clinician as shown in FIG. 5A, and may be provided over user/clinician interface 142, such as described in FIG. 1.

At step 255, it is determined whether the patient is a candidate for surgery; for example, based on these predicted probabilities, an indication or recommendation may be provided to facilitate a patient's or caregiver's decision about whether the patient should undergo a surgical operation or delay. If a decision to receive surgery is made, then method 200 may terminate, and the patient may receive surgery. Some embodiments of method 200 may automatically schedule a patient for surgery based on the outcome of step(s) 250 or 255, or may automatically modify a patient care plan, accordingly If not, then method 200 may also end at step 260 or may be repeated at a future time, as clinically indicated.

With reference now to FIGS. 3-5B, aspects of one example embodiment reduced to practice are illustratively provided. This example embodiment comprises a system and method for providing a multi-variable properties-based prediction of post-operative outcomes after epilepsy surgery.

In the example embodiment, observational data for a period January 2001 through December 2014 were extracted from a confidentiality-protected, HIPAA-compliant, electronic health records-derived datawarehouse (Cerner Health Facts®). Out of a total of 447,905 prevalent epilepsy patients (ICD-9 diagnosis codes 345.xx) in this datawarehouse, there was a cohort 329 surgical patients who were refractory to 2 or more antiepileptic medications, who were treated with neurosurgery (ICD-9 procedure codes 01.3× or 01.5×), and in whom baseline and 1- and 3-year postoperative follow-up data were available with regard to seizure frequency. To serve as controls, an additional 108 refractory epilepsy patients who did not receive surgery but who instead remained on medical antiepileptic drugs were extracted from Health Facts® for the contemporaneous period. Baseline EEG and MRI data were extracted for both the surgical and control groups.

The as-treated dataset contained measurements of the parameters as arose in the course of conventional ordering practices in an ambulatory neurology clinic setting. Therapeutic drug levels of antiepileptic drugs and creatinine were routinely measured on each clinic visit. Surgical procedures were as follows: 210 lesionectomies, 71 disconnecting procedures, 35 polectomies and/or lobectomies, 3 corticectomies and 10 hemispherectomies.

Outcome, measured by postoperative seizure frequency, was analyzed as a function of age at seizure onset, duration of epilepsy, presence of cognitive impairment, lobe of seizure origin, presence of a lesion, histopathology, and completeness of resection. Completeness of resection was defined on the basis of excising both the entire structural lesion if present and the region revealing prominent interictal and ictal abnormalities on intracranial EEG.

Forty-seven percent of patients were seizure-free at 12 months and 89% were seizure-free at 36 months post-op. Lesional status, site of resection, and pathologic diagnoses were not significant predictors of outcome except for in multi-lobar resection, for which overall outcome was inferior (44% class 3 or 4; 22% seizure-free). Completeness of resection was the only significant predictor of good outcome ($p<0.001$), with 92% of patients who underwent complete resection of the epileptogenic zone achieving good outcome compared with 50% of patients who had incomplete resections.

In a subset of 31 patients, interictal high frequency oscillations (HFOs) were available, as a biomarker in epilepsy as well as for defining the seizure-onset zone as for the prediction of the surgical outcome after epilepsy surgery. Properties of HFOs in long-term EEG recordings with respect to the sleep-wake cycle and anatomic regions can be a strongly-influential predictor of clinical context grouping of epileptic patients and a powerful predictor of subsequent surgical outcomes. HFO rates in seizure-onset regional contacts differ from other brain regions independent of the sleep-wake cycle. For temporal lobe contacts, the HFO rate increased significantly with sleep stage. In addition, parietal lobe contacts exhibit a significant increase of HFO rates during sleep. However, no significant HFO rate changes depending on the sleep-wake cycle were found for frontal lobe contacts.

Figure 3:
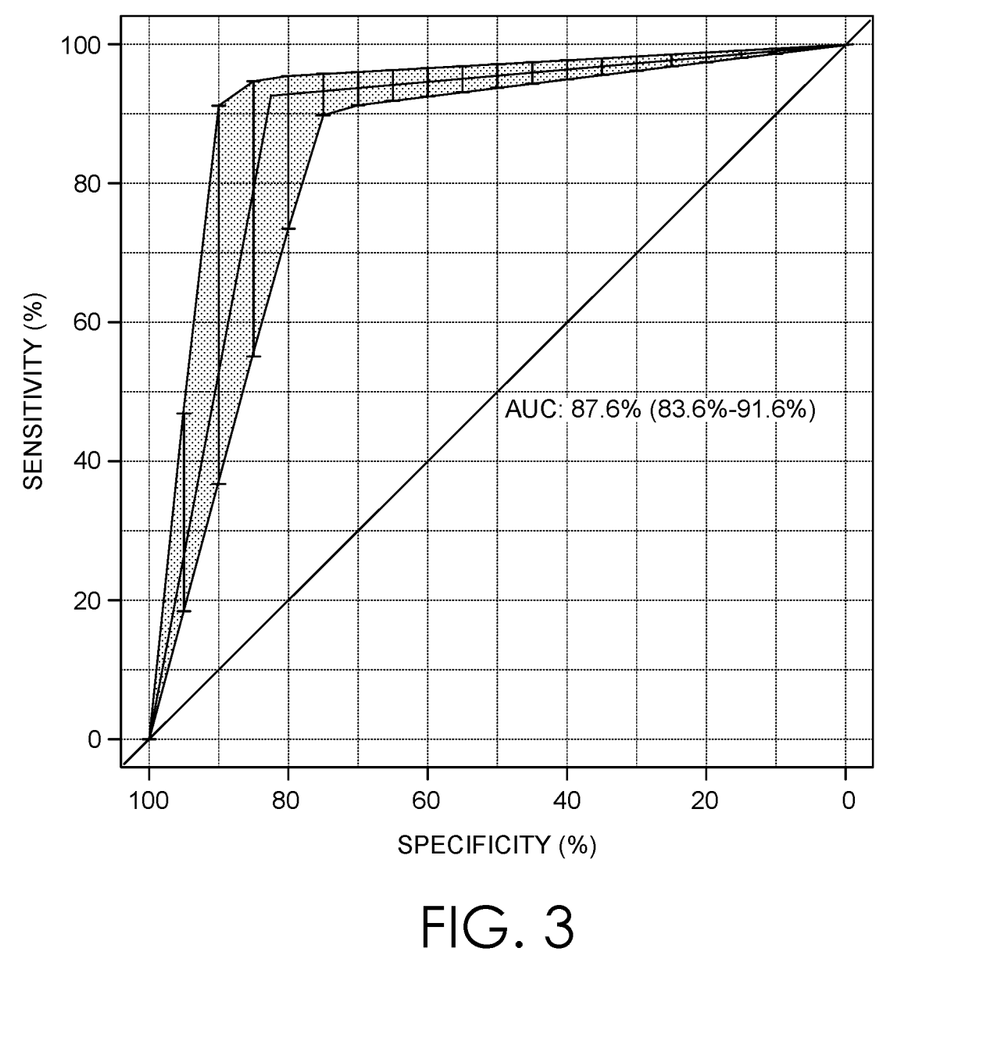
FIG. 3 depicts a Receiver Operating Characteristic (ROC) curve representing the accuracy and discriminating classificatory capacity of the invention in a cohort of 437 subjects, in accordance with an embodiment of the disclosure.

The Random Forest R-package implementation of the Random Forest method was used to identify a subset of parameters whose values were associated with performance of a neurosurgical procedure. Two parameters (positive EEG findings; positive MRI findings) were determined to be statistically significant and were retained for subsequent modeling via multinomial logistic regression. The ROC area under the curve in the final model was 0.88, as shown in FIG. 3.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

Additional embodiments include:

Embodiment 1: Computer-readable media having computer-executable instructions embodied thereon that when executed, facilitate a method for automatically predicting candidacy for epilepsy surgery that is likely to result in clinically beneficial response, the method comprising: obtaining EEG and MRI measurements representative of an individual; detecting the presence of positive findings in the measurements; determining, utilizing an objective function, a risk score from the signals; and determining a plurality of metrics comprising a score and a reference value to classify the likelihood of efficacy of the agent(s) in reducing seizure frequency within a future time interval, wherein a significant difference is indicative of a probability of beneficial response.

Embodiment 2: The computer readable media of embodiment 1, wherein the objective function evaluates digitized multi-variable observations from the one or a plurality of previous time intervals to classify the likelihood of response of the patient's epilepsy to a neurosurgical procedure within a future time interval.

Embodiment 3: The systems of any of embodiments 1-2, wherein the objective function comprises a plurality of metrics including comorbid conditions.

Embodiment 4: The systems of any of embodiments 1-3, wherein the results of the objective function are used by a decision-support algorithm to determine a quantitative likelihood of future seizure frequency, as assessed by Engel Class or other suitable measures, or, alternatively, the quantitative likelihood of mitigation of the seizure by a neurosurgical procedure or by continued medical management with antiepileptic medications.

Embodiment 5: The systems of any of the embodiments 1-4, wherein the decision-support algorithm is a statistical model that combines a plurality of measures for surgical efficacy comprising at least one resectability measure.

Embodiment 6: Computer-readable media having computer-executable instructions embodied thereon that when executed, facilitate a method for determining a surgery candidacy score for an individual, the method comprising: identifying biomarker signals representative of changes in seizure frequency of an individual having epilepsy; and determining a surgical candidacy score based on measurements made at a plurality of times, for determining a likelihood of seizure frequency within a future time interval of up to 36 months from the time of the most recent measurement.

Embodiment 7: The media of embodiment 6, wherein determining temporal properties of each biomarker's serial measurements time series further comprises eliminating anomalous biomarker values from subsequent processing.

Embodiment 8: A time series calculation apparatus utilizing embodiment 1, wherein the means involves calculations by difference equation or regression methods, or a plurality of these calculated jointly, and storing the results in computer-readable media.

Embodiment 9: Any of embodiments 1-8, wherein the method further comprises transforming the signals via threshold comparisons or other mathematical transformation of each variable prior to determining a composite surgical candidacy score.

Embodiment 10: Any of embodiments 1-9, wherein the determining a surgical candidacy score based on the temporal properties further comprises establishing a baseline surgical candidacy score pertaining to members of an epileptic population about whom two or more measurements have not yet been acquired or are pending.

Embodiment 11: Any of embodiments 1-10, wherein the determining a surgical candidacy score based on the biomarkers time series further comprises computing a predicted probability of responsiveness to a neurosurgical procedure via a generalized linear model such as a multinomial logistic regression or probit regression, decision-tree induction, artificial neural network, support vector machine, or other classification algorithm.

Embodiment 12: Any of embodiments 1-11, wherein said determining a surgical candidacy score based on the biomarkers time series further comprises calculating and storing a plurality of timeseries metrics and combining the evidence from such an ensemble comprised of the plurality of ensemble member tests, so as to achieve a higher accuracy than would be possible for any single test.

Embodiment 13: A method for automatically predicting surgical candidacy or neurosurgical therapy responsiveness in humans the method comprising: obtaining biomarker measurements representative of an individual; determining, utilizing an objective function, a surgical candidacy score from said signals based on one or a plurality of time intervals, to classify a likelihood of seizure frequency (such as Engel Class) within a future time interval; and determining a difference between the score or probability and respective reference values for these, wherein a significant difference is indicative of an statistically and clinically significant disparities between medical and neurosurgical interventions' outcomes such as to warrant preventive or therapeutic intervention.

Embodiment 14: The method of embodiment 13, wherein the objective function evaluates persisting computer-readable media containing timeseries records in an electronic health record system from one or a plurality of previous time intervals to classify the likelihood of seizure frequency within a future time interval.

Embodiment 15: The methods of any of embodiments 13-14, wherein the objective function comprises a timeseries calculated from serially-acquired acceleration data embodying a plurality of biomarker timeseries temporal properties as functions of time where the calculated time series are stored in persisting computer-readable media for usage in later display, printing, or decision-support functions.

Embodiment 16: The methods of any of embodiments 13-15, wherein the results of the objective function are used by a decision-support algorithm to determine a quantitative likelihood of seizure frequency at future time intervals subsequent to medical and neurosurgical treatments.

Embodiment 17: The methods of any of embodiments 13-16, wherein the decision-support algorithm comprises an ensemble model predictive algorithm that combines evidence from the results of a plurality of tests to establish a preponderant tendency or overall probabilities of different seizure frequency levels or categories.

Embodiment 18: The methods of any of embodiments 13-17, wherein the method further comprises providing a notification to a health care provider when the difference in medical versus neurosurgical outcomes' probabilities ought to inform the therapeutic decisions and guide which therapy alternative(s) is (are) recommended.

Embodiment 19: The methods of any of embodiments 13-18, wherein the reference value is determined based on parameters associated with the individual including at least one age, seizure etiology, epileptogenic focus location, epileptogenic focus laterality, and seizure frequency history; wherein the determined difference is determined as significant when the difference exceeds a threshold or imparts membership in a set or grouping of patients; and wherein the threshold or set-membership is based on a value indicative of minor fluctuations in activity level of the individual.

Embodiment 20: Any of embodiments 1-5, wherein the reference value is determined based on parameters associated with the individual including at least one of age, seizure etiology, epileptogenic focus location, epileptogenic focus laterality, and seizure frequency history; wherein the determined difference is determined as significant when the difference exceeds a threshold or imparts membership in a set or grouping of patients; and wherein the threshold or set-membership is based on a value indicative of epilepsy context of the individual.

Embodiment 21: Any of embodiments 1-5 or 20, wherein the measurement methods for each biomarker may be either via electroencephalogram or electrocorticography testing methods and apparatus or magnetic resonance or other diagnostic imaging methods and apparatus.

Embodiment 22: Any of embodiments 1-5 or 20-21, wherein the transmittal of the measured biomarker values is performed online by means of computer interface software and network communications media with an electronic health record system or laboratory information system apparatus.

Embodiment 23: Any of embodiments 1-5 or 20-22, wherein the decision-support processing involves automated invocation of prescriptions or orders pertaining to managing epilepsy, based on set-membership or threshold transgressions of the embodiments.

What is claimed is:

1. A computerized method of determining candidacy for neurological surgery, the computerized method comprising:
   determining, by a processor coupled to a memory, a first seizure frequency for a patient at a first time and a second seizure frequency for the patient at a second time, the first time and the second time separated by a time period, wherein a plurality of patient information is retrieved from one or more electronic health record storage systems distributed across multiple physical location and one or more monitors, wherein disparate health systems' ontologies are mapped on the plurality of patient-information to generate the first seizure frequency for the patient at the first time and the second seizure frequency for the patient at the second time and the mapped patient information is stored in memory, wherein the processor is communicatively coupled through a computer network to the one or more monitors comprising one or more sensor components operable to acquiring physiologic information;
   continuously receiving and mapping with the disparate health systems' ontologies, by the processor, real-time patient information from the one or more monitors and the one or more electronic health storage systems, wherein the mapped real-time patient information is stored in the memory, and wherein the mapped real-time patient information is stored in the one or more electronic health record storage systems and communicated via one or more user computer interface providing one or more users access to the mapped real-time patient information;

determining, by the processor, an epileptogenic focus or etiology of a structural abnormality identified from a neurodiagnostic test performed on the patient;

determining, by the processor, a resectability of the epileptogenic focus or etiology and a secondary comorbid condition, wherein the secondary comorbid condition is present in the patient and was found to have statistical impact on a final probability outcome of the neurological surgery;

assigning, by the processor, an applicable context-specific group based on the resectability of the epileptogenic focus or etiology and the secondary comorbid conditions;

assigning, by the processor, a classification model corresponding to the applicable context-specific group, the classification model trained on observational data for a historical cohort of neurosurgical patients having post-operative seizure frequency data;

determining, by the processor, a first predicted probability of improvement associated with patient surgery using the assigned classification model based on an improvement in seizure frequency over the first seizure frequency and the second seizure frequency;

determining, by the processor, a second predicted probability of improvement associated with delaying the patient surgery using the assigned classification model based on an improvement in seizure frequency over the first seizure frequency and the second seizure frequency; and providing, by the processor, an indication of the first predicted probability of improvement associated with the patient surgery and an indication of the second predicted probability of improvement associated with delaying patient surgery, and wherein the indications are provided via a graphical user interface of a computing device of one or more of the patient, a caregiver associated with the patient, and a clinician.

2. The computerized method of claim 1, wherein the context-specific group comprises an Engle Class.

3. The computerized method of claim 1, wherein the neurodiagnostic test comprises an electroencephalogram (EEG) or a magnetic resonance imaging (MRI) scan.

4. The computerized method of claim 1, wherein the time period comprises at least three months.

5. The computerized method of claim 1, wherein the classification model uses logistic regression.

6. The computerized method of claim 1, wherein the indication of the predicted probability of improvement comprises a probability of improvement having undergone the patient surgery or a probability of improvement when delaying the patient surgery, and wherein the indication is provided over a graphical user interface presented to the patient or a caregiver associated with the patient.

7. The computerized method of claim 1, wherein the first seizure frequency and the second seizure frequency are determined using the one or more sensors that detects patient seizures.

8. One or more computer-readable media having computer-usable instructions embodied thereon that, when executed, enable a given processor to perform a method of determining candidacy for neurological surgery, the method comprising:

determining a first seizure frequency for a patient at a first time and a second seizure frequency for the patient at a second time, the first time and the second time separated by a time period, wherein a plurality of patient information is retrieved from one or more electronic health record storage systems distributed across multiple physical location and one or more monitors, and disparate health systems' ontologies are mapped on the plurality of patient information to generate the first seizure frequency for the patient at the first time and the second seizure frequency for the patient at the second time and the mapped patient information is stored in memory, wherein the processor is communicatively coupled through a computer network to the one or more monitors comprising one or more sensor components operable to acquiring physiologic information;

continuously receiving and mapping with the disparate health systems' ontologies, real-time patient information from the one or more monitors and the one or more electronic health storage systems, wherein the mapped real-time patient information is stored in the memory, and wherein the mapped real-time patient information is stored in the one or more electronic health record storage systems and communicated via one or more user computer interface providing one or more users access to the mapped real-time patient information;

determining an epileptogenic focus or etiology of a structural abnormality identified from a neurodiagnostic test performed on the patient;

determining a resectability of the epileptogenic focus or etiology and a secondary comorbid condition, wherein the secondary comorbid condition is present in the patient and was found to have statistical impact on a final probability outcome of the neurological surgery;

assigning an applicable context-specific group for the patient based on the resectability of the epileptogenic focus or etiology and the secondary comorbid condition; assigning a classification model corresponding to the applicable context-specific group, the classification model trained on observational data for a historical cohort of neurosurgical patients having post-operative seizure frequency data;

determining a first predicted probability of improvement associated with patient surgery using the assigned classification model based an improvement in seizure frequency over the first seizure frequency and the second seizure frequency;

determining a second predicted probability of improvement associated with delaying the patient surgery using the assigned classification model based on an improvement in seizure frequency over the first seizure frequency and the second seizure frequency; and providing an indication of the first predicted probability of improvement associated with the patient surgery and an indication of the second predicted probability of improvement associated with delaying patient surgery, and wherein the indications are provided via a graphical user interface of a computing device of one or more of the patient, a caregiver associated with the patient, and a clinician.

9. The media of claim 8, wherein the applicable context-specific group comprises an Engle Class.

10. The media of claim 8, wherein the neurodiagnostic test comprises an electroencephalogram (EEG) or a magnetic resonance imaging (MRI) scan.

11. The media of claim 8, wherein the indication of the predicted probability of improvement comprises a probability of improvement having undergone the patient surgery or a probability of improvement when delaying the patient surgery.

12. The media of claim 8, wherein the assigned classification model uses logistic regression.

13. The media of claim 8, further comprising generating a recommendation for the patient surgery or automatically scheduling the patient surgery.

14. The media of claim 8, wherein the indication of the predicted probability of improvement is provided over a graphical user interface presented to the patient or a caregiver associated with the patient.

15. A computerized system comprising:
one or more sensors configured to determine seizure frequency for a patient;
one or more processors; and
computer storage memory having computer-executable instructions stored thereon which, when executed by the processor, cause the one or more processors to implement a method of determining candidacy for neurological surgery, the method comprising:
determining, from the one or more sensors, a first seizure frequency for a patient at a first time and a second seizure frequency for the patient at a second time, the first time and the second time separated by a time period, wherein a plurality of patient information is retrieved from one or more electronic health record storage systems distributed across multiple physical location and the one or more sensors, and disparate health systems' ontologies are mapped on the plurality of patient information to generate the first seizure frequency for the patient at the first time and the second seizure frequency for the patient at the second time;
continuously receiving and mapping with the disparate health systems' ontologies, real-time patient information from the one or more sensors and the one or more electronic health storage systems, wherein the mapped real-time patient information is stored in the memory, and wherein the mapped real-time patient information is stored in the one or more electronic health record storage systems and communicated via one or more user computer interface providing one or more users access to the mapped real-time patient information;
determining an epileptogenic focus or etiology of a structural abnormality identified from a neurodiagnostic test performed on the patient;
determining a resectability of the epileptogenic focus or etiology and a secondary comorbid condition;
assigning an applicable context-specific group for the patient based on the resectability of the epileptogenic focus or etiology and the secondary comorbid condition, wherein the secondary comorbid condition is present in the patient and was found to have statistical impact on a final probability outcome of the neurological surgery;
assigning a classification model corresponding to the applicable context-specific group, the classification model trained on observational data for a historical cohort of neurosurgical patients having post-operative seizure frequency data;
determining a first predicted probability of improvement associated with patient surgery using the assigned classification model based on an improvement in seizure frequency over the first seizure frequency and the second seizure frequency;
determining a second predicted probability of improvement associated with delaying patient surgery using the assigned classification model based on an improvement in seizure frequency over the first seizure frequency and the second seizure frequency; and
providing an indication of the first predicted probability of improvement associated with the patient surgery and an indication of the second predicted probability of improvement associated with delaying patient surgery, and wherein the indications are provided via a graphical user interface of a computing device of one or more of the patient, a caregiver associated with the patient, and a clinician.

16. The system of claim 15, wherein the applicable context-specific group comprises an Engle Class.

17. The system of claim 15, wherein the neurodiagnostic test comprises an electroencephalogram (EEG) or a magnetic resonance imaging (MRI) scan, and wherein the assigned classification model uses logistic regression.

18. The system of claim 15, further comprising generating a recommendation for the patient surgery or automatically scheduling the patient surgery.

19. The system of claim 15, wherein the indication of the predicted probability of improvement comprises a probability of improvement having undergone the patient surgery or a probability of improvement when delaying the patient surgery.

20. The system of claim 19, wherein the indication of the predicted probability of improvement is provided over a graphical user interface presented to the patient or a caregiver associated with the patient.

* * * * *

UNITED STATES PATENT AND TRADEMARK OFFICE
CERTIFICATE OF CORRECTION

| | |
|---|---|
| PATENT NO. | : 11,357,444 B1 |
| APPLICATION NO. | : 15/294299 |
| DATED | : June 14, 2022 |
| INVENTOR(S) | : Douglas S. McNair |

It is certified that error appears in the above-identified patent and that said Letters Patent is hereby corrected as shown below:

In the Specification

Column 5, Line 22:
"patients' and the clinicians' decision-making In other words," should read --patients' and the clinicians' decision-making. In other words,--

Column 12, Line 56:
"care plan, accordingly If not, then method 200 may also end" should read --care plan, accordingly. If not, then method 200 may also end--

Signed and Sealed this
Thirtieth Day of August, 2022

*Katherine Kelly Vidal*

Katherine Kelly Vidal
*Director of the United States Patent and Trademark Office*